United States Patent
Eisenhut et al.

(10) Patent No.: US 7,988,892 B2
(45) Date of Patent: Aug. 2, 2011

(54) PREPARATION AND STERILIZATION OF GREEN STATE DEVICES USING A SUPERCRITICAL FLUID STERILANT

(75) Inventors: Anthony R. Eisenhut, Lansing, NY (US); J. Anastasia Kazenski, Ithaca, NY (US); Renee A. Christopher, Dryden, NY (US)

(73) Assignee: Novasterilis, Lansing, NY (US)

( * ) Notice: Subject to any disclaimer, the term of this patent is extended or adjusted under 35 U.S.C. 154(b) by 2 days.

(21) Appl. No.: 12/277,425

(22) Filed: Nov. 25, 2008

(65) Prior Publication Data

US 2009/0134542 A1    May 28, 2009

Related U.S. Application Data

(60) Provisional application No. 60/996,595, filed on Nov. 27, 2007.

(51) Int. Cl.
*A61L 2/16* (2006.01)
*B29C 37/00* (2006.01)

(52) U.S. Cl. ........ 264/82; 264/40.3; 264/40.5; 264/109; 264/122; 422/28; 422/33; 419/66

(58) Field of Classification Search .................. 264/40.3, 264/40.5, 82, 83, 109, 122; 422/28, 33; 419/66
See application file for complete search history.

(56) References Cited

U.S. PATENT DOCUMENTS

| | | | | |
|---|---|---|---|---|
| 4,996,024 | A * | 2/1991 | Nishio et al. | 419/40 |
| 5,215,697 | A * | 6/1993 | Toki et al. | 264/121 |
| 5,422,377 | A * | 6/1995 | Aubert | 521/64 |
| 6,149,864 | A * | 11/2000 | Dillow et al. | 422/28 |
| 6,506,213 | B1 * | 1/2003 | Mandel et al. | 623/16.11 |
| 6,620,356 | B1 * | 9/2003 | Wong et al. | 264/41 |
| 7,108,832 | B2 * | 9/2006 | Christensen et al. | 422/28 |
| 7,160,492 | B2 * | 1/2007 | King | 264/101 |

* cited by examiner

*Primary Examiner* — Richard Crispino
*Assistant Examiner* — Robert Dye
(74) *Attorney, Agent, or Firm* — Welsh, Flaxman & Gitler LLC

(57) ABSTRACT

The invention relates to a method for forming a molded article during sterilization and under high pressure utilizing a supercritical fluid as a sterilization fluid, whereby the pressurization and depressurization rates are controlled to form molded articles.

15 Claims, 1 Drawing Sheet

Figure 1:
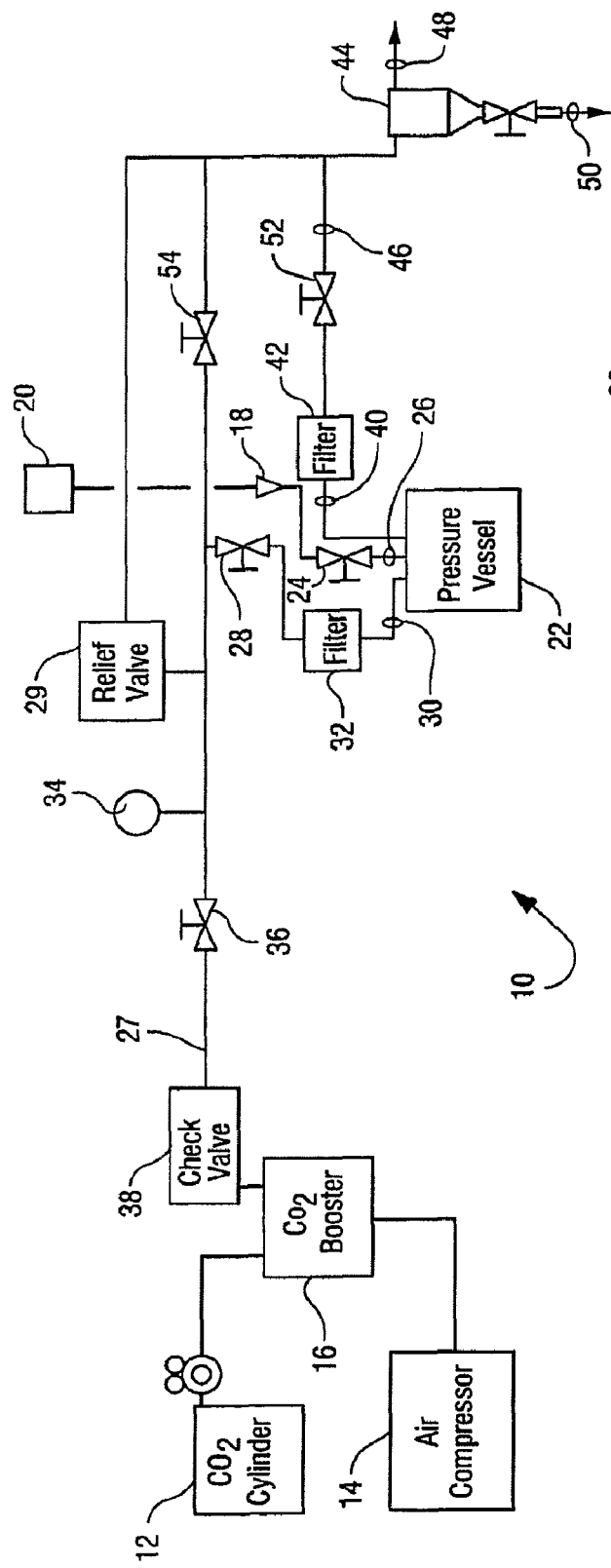

PREPARATION AND STERILIZATION OF GREEN STATE DEVICES USING A SUPERCRITICAL FLUID STERILANT

CROSS REFERENCE TO RELATED APPLICATIONS

This application claims the benefit of U.S. Provisional Application Ser. No. 60/996,595, entitled "Preparation and Sterilization of Green State Devices Using a Supercritical Fluid Sterilant", filed Nov. 27, 2007.

FIELD OF THE INVENTION

The present invention relates generally to a method of forming a molded article preferably during sterilization under high pressure utilizing a supercritical fluid as a sterilization fluid, whereby the pressurization and depressurization rates are controlled to form molded articles.

BACKGROUND OF THE INVENTION

The orthopedic device market has annual revenues in excess of a billion dollars in the United States alone. Biomedical companies produce orthopedic devices from polymeric and animal derived materials, such as DBM (demineralized bone matrix) powder and bone cement.

Such medical appliances are normally manufactured via chemical and thermal forming processes. Specifically, certain biological and polymeric materials are unable to withstand intense heat and their physical properties are significantly altered to a point where they are unstable, and in extreme cases, ultimately vaporize at elevated temperatures. Thus, when heat sensitive compounds are employed in the manufacture of medical devices, the use of heated molds, heated pourable forms and casts can be problematic.

Many medical devices, such as stents, catheters and endoscopes, are fabricated from, or coated with, sensitive polymers that cannot tolerate steam, irradiation, or ethylene oxide. Many new medical advances cannot be implemented because the sterilization industry is unable to provide a suitable sterilant as part of the manufacturing process. Plasma sterilization has been shown to be incompatible with some medical equipment and leaves toxic residues. Thus there is a need for a gentle and reliable sterilization method that results in greater than a 6-log reduction of microbial and viral contaminants in the material to be sterilized without deleteriously impacting the properties of the material being sterilized.

Recently, in U.S. Pat. No. 6,149,864 to Dillow et al. (the entire content of which is expressly incorporated hereinto by reference), the use of supercritical $CO_2$ was disclosed as an alternative to existing technologies for sterilizing a wide range of products for the healthcare industry with little or no adverse effects on the material treated. Specifically, the Dillow '864 patent disclosed the inactivation of a wide range of vegetative microbial cells using supercritical carbon dioxide with agitation and pressure cycling. However, only one spore-forming bacterium was investigated in the Dillow '864 patent, specifically, $B.\ cereus$. No disclosure appears in Dillow et al. '864 patent regarding the efficacy of the therein suggested techniques using currently accepted bio-indicator standards used to judge sterilization (i.e., $B.\ stearothermophilus$ and $B.\ subtilis$). Subsequently, however, other investigators achieved only a 3.5 log reduction in $B.\ subtilis$ spores using the method disclosed in the Dillow et al. '864 patent.

Even more recently, in U.S. Pat. No. 7,108,832 to Christensen et al. (the entire content of which is expressly incorporated hereinto by reference), the use of supercritical $CO_2$ was disclosed as an alternative to existing technologies for sterilizing a wide range of products for the healthcare industry with little or no adverse effects on the material treated.

Bacterial spores are more difficult to sterilize than vegetative cells. $B.\ stearothermophilus$ and $B.\ subtilis$ spores represent the greatest challenge to sterilization methods (FDA 1993) and are the currently accepted standards within the industry for validating sterilization methods. Sterilization is defined as greater than or equal to a 6-log ($10^6$) reduction in colony forming units (CFUs). Reproducible inactivation of these resistant microbes is required for commercialization of novel sterilization equipment and processes.

It would be highly desirable to develop a process for the manufacture of medical devices, such as implants, formed from green state materials utilizing a single step method resulting in the hardening of the material into a solid cast without exposure to the deleterious effects of heat. It would also be highly desirable to develop a process for the manufacture of medical devices, such as implants, formed from green state materials utilizing a single step method resulting in the simultaneous hardening and sterilization of the material into a solid cast. It is desirable to perform a simultaneous sterilization during the molding of the green materials to produce a formed medical device, such as an implant, that achieves a 6-log reduction in CFUs. The present invention is therefore directed to fulfilling such needs.

SUMMARY OF THE INVENTION

The present invention is directed to a single step method resulting in the simultaneous hardening and sterilization of a green state material into a solid cast. A sterilization method is provided that is effective in achieving a 6-log reduction in CFUs of industry standard bacterial spores when treating processable green state material in any physical form, preferably powder form. More specifically, a sterilization method is provided which is effective in achieving a 6-log reduction in CFUs of $B.\ stearothermophilus$ and $B.\ subtilis$ spores. These 6-log reductions are achieved with the present invention by subjecting sterilizable materials under controlled sterilization pressure and temperature conditions using a chemical additive-containing supercritical fluid including but not limited to carbon dioxide as a sterilant fluid. Most preferably, the chemical additive-containing supercritical carbon dioxide sterilant fluid is agitated during sterilization.

It is an object of the present invention to provide a combined sterilization and solidification process comprising (a) placing a green state material in any physical form, preferably a micro-crystalline or powder form, in need of sterilization in a mold with a sterilization enhancing effective amount of a chemical sterilization additive, (b) regulating the pressurization rate of the mold to bring the green state material into contact with a sterilant fluid at or near its supercritical pressure and temperature conditions, (c) maintaining the contact with the sterilant fluid under the temperature and pressure conditions for a time sufficient to achieve a 6-log reduction or greater in colony forming units (CFUs), and then (d) regulating the depressurization rate of the mold until ambient operating conditions are reached, so that by regulating the pressurization and depressurization rates, the green state material is hardened or solidified into a sterilized, solid object.

It is also a further object of the present invention to provide a combined sterilization and solidification process wherein the chemical sterilization additive is selected from the group consisting of hydrogen peroxide, acetic acid, peracetic acid and trifluoroacetic acid and/or a mixture thereof.

It is yet another object of the present invention to provide a combined sterilization and solidification process applicable to green state materials wherein the step of regulating the pressurization rate of the vessel occurs at least 5 psi per second until operating conditions are reached and the step of regulating the depressurization rate of the mold or vessel until ambient operating conditions are reached occurs at least 5 psi per second.

It is a further object of the present invention to provide a combined sterilization and solidification process wherein the sterilization additive is present in an amount of between about 0.001% to about 2.0% based on the total volume of the sterilant fluid.

It is still a further object of the present invention to provide a combined sterilization and solidification process wherein pressurization occurs until about 1100 psi to about 3500 psi is reached. A pressure and temperature must be attained to transform the treating fluid into its supercritical state.

It is also an object of the present invention to provide a combined sterilization and solidification process wherein the pressure is maintained at least at about 1100 psi for 20 to 720 minutes followed by regulated depressurization.

It is also another object of the present invention to provide a combined sterilization and solidification process wherein depressurization occurs at a rate of at least 5 psi per second until ambient conditions are reached.

It is also another object of the present invention to provide a solidification process having the ability to process heat sensitive biopolymers or other materials in a molding fashion while eliminating the factors that cause rejection of such a material in a human body.

These and other aspects and advantages will become more apparent after careful consideration is given to the following detailed description of the preferred exemplary embodiments thereof.

BRIEF DESCRIPTION OF THE ACCOMPANYING DRAWINGS

Figure 2:
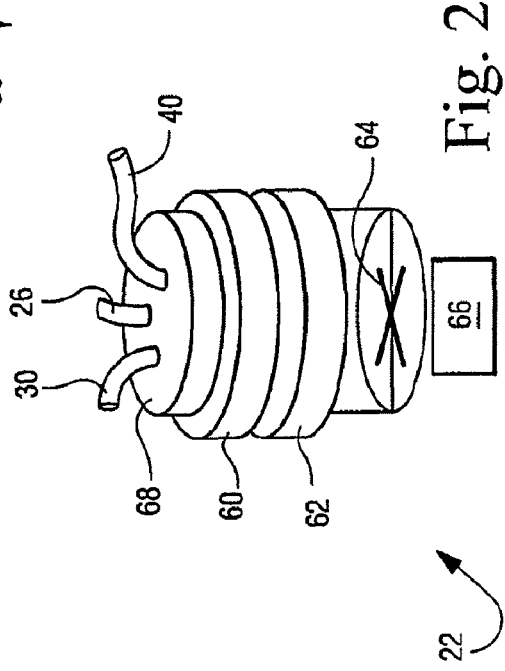

Reference will hereinafter be made to the accompanying drawings, wherein like reference numerals throughout the various FIGURES denote like structural elements, and wherein;

FIG. 1 is a schematic view of a presently preferred combined sterilization and solidification apparatus in accordance with the present invention; and FIG. 2 is a detailed schematic view of the pressure mold or vessel employed in the apparatus of FIG. 1.

DETAILED DESCRIPTION OF THE INVENTION

The present invention relates to a method for solidifying and sterilizing implantable biomaterials utilizing a supercritical fluid treatment, preferably utilizing carbon dioxide as the supercritical fluid; however, other supercritical fluids such as nitrogen, for example, can be used in the present invention. While the use of other supercritical fluids is contemplated in the process of the present invention, the following discussion will be limited to the use of carbon dioxide in the process for purposes of example only. The process treats heat sensitive biomaterials in a molding fashion while simultaneously sterilizing the biomaterials thereby eliminating the factors that cause rejection by the human body. The supercritical carbon dioxide treatment of the present invention effectively functions as a non-toxic, relatively low temperature process by which bone cement or other materials in their "green state" can be solidified in a single step. The supercritical carbon dioxide treatment effectively functions as a successful method for the sterilization, decontamination, cleaning and molding by solidification of bone cement or other "green state" biomaterials. The created solid, preferably in the form of an implant, from the mold must be able to be effectively implanted into humans. When desired, such a substance preferably has the ability to allow the formation and migration of bone tissue newly formed by the recipient.

The most common current technique for producing a desired shape is to heat a substance to its melting point and pour the liquid compound into a mold. By use of the present invention it is thus possible to have compounds which are unable to withstand intense heat, complete solidification and create any shape or form desired.

Currently the method by which bone cement is solidified includes the use of chemicals such as methyl methacrylate-copolymer for strength, polymethyl methacrylate (PMMA) for handling, and barium sulphate for radioopaqueness. The supercritical carbon dioxide process eliminates the need for all of these previously listed compounds by utilizing a single step to produce a hard, sterile substance formed in a safe, non-toxic manner.

In order to perform the molding process of the present invention it is necessary to obtain conditions in the mold so that the supercritical fluid is at a sufficient temperature and pressure to achieve and maintain its supercritical state. One of the advantages of the invention lies in the preferable use of carbon dioxide as a fluid in the supercritical state, because this constituent has many advantageous properties i.e., its critical temperature, 31° C., is low. Carbon dioxide achieves the supercritical state at 31° C. at 1098 psi.

The sterilization apparatus and methods of the present invention are usefully employed to sterilize a variety of materials, biological tissues, instruments, and devices that are thermally or hydrolytically unstable, or otherwise incompatible with conventional sterilization techniques, or where such techniques are not preferred. Examples of materials that may be sterilized by the present invention include, but are not limited to, metal powders; ceramic/glass powders, including but not limited to: alumina, calcium phosphate, calcium carbonate, hydroxyapatite, silica, silicates and borosilica; polymers including but not limited to form factors including powder, slurry, solution, pellet, film formed from polylactide (PLA), polyglycolide (PGA), poly(lactide-co-glycolide) (PLGA), poly(e-caprolactone), polydioxanone, polyanhydride, dimethylene carbonate, poly(B-hydroxybutyrate) (PHB), poly(g-ethylglutamate), poly(DTH iminocarbonate), poly(bisphenol A iminocarbonate), poly(ortho ester), polycyanoacrylate, polyphosphazene, ethylene oxide block copolymers, polysaccharides such as cellulose, chitin or dextran, natural polymers such as fibrin, collagen, gelatin, hyaluronan or casein, polycarbonate, and poly(HEMA); monomers; resins; demineralized bone matrix; crystalline small molecules (drugs); as well as mixtures thereof.

Selective materials can be used in various embodiments as implantable drug delivery devices; tissues for implantation or transplantation, including but not limited to, bone, cartilage, ligament, or other connective or musculoskeletal tissue for allografts in the treatment of orthopaedic trauma and joint reconstruction; grafted or artificial skin tissue for the treatment of burns and other dermal abrasions or damage; medical devices, such as cardiac or urological stents and catheters, including drug- or gene-coated stents and catheters, rigid and flexible endoscopes for orthopaedic, plastic, and gastroenterological surgery; drug delivery devices, including, but not limited to, implantable polymer devices, polymer microspheres, or other specifically shaped drug-releasing devices comprised of PLA, PLGA, or other biodegradable polymers, and drugs in solid including but not limited to micro-crystalline and powder forms or liquid forms (i.e., any substance or active agent used in the diagnosis, treatment or prevention of a disease or illness).

As noted previously, 6-log reductions in CFUs may be achieved in accordance with the present invention by subjecting materials to be sterilized and solidified under sterilization and molding temperature and pressure conditions using a chemical additive-containing supercritical carbon dioxide as a sterilant fluid, and especially where the sterilant fluid is agitated during the sterilization process.

Most preferably, the sterilant is carbon dioxide at or near its supercritical pressures and temperature conditions. Thus, the sterilization process of the present invention is practiced using carbon dioxide as a sterilant at pressures between about 1100 psi to about 3500 psi, at temperatures in the range between about 25° C. to about 60° C. Most preferably, the article to be sterilized is subject to carbon dioxide at or near such pressure and temperature conditions for times ranging from about 20 minutes to about 12 hours. The carbon dioxide employed in the practice of the present invention is most preferably substantially pure. Thus, trace amounts of other gases may be tolerated provided that the sterilization properties of the carbon dioxide are not impaired. For ease of further discussion below, the term "supercritical carbon dioxide" will be used, but it will be understood that such a term is non-limiting in that carbon dioxide within the pressure and temperature ranges as noted immediately above may be employed satisfactorily in the practice of the present invention.

The chemical additives that may be employed in conjunction with the supercritical fluid in the present invention most preferably include peroxides and/or carboxylic acids. Preferred carboxylic acids include alkanecarboxylic acids and/or alkanepercarboxylic acids, each of which may optionally be substituted at the alpha carbon with one or more electron-withdrawing substituents, such as halogen, oxygen and nitrogen groups. Particularly preferred species of chemical additives employed in the practice of the present invention include hydrogen peroxide ($H_2O_2$), acetic acid (AcA), peracetic acid (PAA) and trifluoroacetic acid (TFA), and mixtures thereof. One particularly preferred liquid additive that may be employed in the practice of the present invention is commercially available Sporeclenz® sterilant, which is a mixture of acetic acid with hydrogen peroxide and peracetic acid.

The chemical sterilization additive is employed in a sterilization enhancing effective amount of at least about 0.001 vol % and greater, based on the total volume of the carbon dioxide. The amount of sterilization additive will be dependent upon the particular sterilization additive that is employed. Thus, for example, peracetic acid may be present in relatively small amounts of about 0.005 vol % and greater, while acetic acid may need to be employed in amount of about 1.0 vol % and greater. Thus, a range of at least about 0.001 vol % and greater, up to about 2.0 vol % will typically be needed in order to achieve a sterilization enhancing effect in combination with carbon dioxide.

Additionally mold processing aids known to those skilled in the art can be added to the charge in the mold together with the moldable "green state" materials to improve cohesiveness of the formed article and its release from the mold.

The presently preferred embodiment of an apparatus 10 according to the present invention is depicted in accompanying FIGS. 1 and 2. In this regard, it can be seen that the apparatus includes a standard compressed gas cylinder 12 containing carbon dioxide, and a standard air compressor 14 used in operative association with a carbon dioxide booster 16 (e.g., Haskel Booster AGT 7/30). Alternatively, the air compressor 14 and carbon dioxide booster 16 can be replaced with a single carbon dioxide compressor.

An additive cycle is also provided by means of an inlet port 18 which allows additive contained in reservoir 20 to be added to a mold reactor pressure vessel 22 through valve 24 and additive line 26. The carbon dioxide is introduced to the mold reactor 22 from header line 27 via valve and regulator (herein called valve 28) and $CO_2$ supply line 30. A filter 32 (e.g., a 0.5 micron filter) is provided in the supply line 30 to prevent the escape of material from the mold reactor. A pressure gauge 34 is provided downstream of $CO_2$ shut-off valve 36 in supply header line 27 to allow the pressure to be visually monitored. A check valve 38 is provided in the header line 27 upstream of the $CO_2$ shut-off valve 36 to prevent reverse fluid flow into the carbon dioxide booster 16. In order to prevent an overpressure condition existing in header line 27, a pressure relief valve 9 may be provided.

An outlet line 40 through valve and regulator (herein called valve 52) allows mold reactor 22 to be depressurized. In this regard, the depressurized fluid exits the reactor pressure vessel 22 via outline line 40, is filtered by filter unit 42 and then is directed to separator 44 where filtered $CO_2$ gas may be exhausted via line 48, and liquid additive collected via line 50 for possible reuse. Valves 52, 54 may be provided in lines 46 and 27, respectively, to allow fluid isolation of upstream components. The mold reactor 22 is most preferably constructed of stainless steel (e.g., 316 gauge stainless steel) and has a total internal volume sufficient to accommodate the materials being solidified and sterilized either on a laboratory or commercial scale. For example, in laboratory studies, an internal volume of 600 mL (e.g., approximately 8 inches long by about 2.5 inches inside diameter) was deemed adequate As is perhaps more clearly shown in FIG. 2, the mold reactor 22 includes a vibrator 60, a temperature control unit 62, and a mechanical stirring system most preferably comprised of an stirring impeller 64 and a magnetic driver 66.

The mold reactor 22 may be operated at a constant pressure or under continual pressurization and depressurization (pressure cycling) conditions without material losses due to splashing or turbulence, and without contamination of pressure lines via back diffusion. The valves 24, 28 and 52 allow the mold reactor pressure vessel 22 to be isolated and removed easily from the other components of the apparatus 10. The top 68 of the mold reactor 22 may be removed when depressurized to allow access to the mold reactor's interior.

In use, the material to be sterilized and solidified is introduced into the interior space of the mold reactor 22 along with any initial portion of liquid sterilization additive from reservoir 20 or an additive pad. The material to be molded is placed in a mold (not shown) to be placed in the mold reactor. In the preferred embodiment the mold is porous or perforated and lined with a porous material to allow contact of the supercritical fluid with the moldable material while containing the material in the mold. A porous material that is unaffected by exposure to supercritical fluid is suitable for lining the mold.

The temperature control unit 62 is operated so as to set the desired initial temperature for sterilization. The mold reactor 22 may then be pre-equilibrated with carbon dioxide from gas cylinder 12 at atmospheric pressure, following which the magnetic driver 66 is operated so as to activate the stirring impeller 64. The mold reactor 22 may thereafter be pressurized to a desired pressure by introducing additional carbon dioxide gas from gas cylinder 12 via the air compressor 14 linked to carbon dioxide booster 16.

In order to affect a pressure cycling of the mold reactor 22, an amount of carbon dioxide may be released therefrom via depressurization outline line 40 by momentarily opening valve 52 sufficient to partially reduce pressure within the mold reactor 22. Additive may be introduced into the mold reactor 22 for any given pressure cycle by opening valve 24 which allows liquid additive to flow from reservoir 20 into inlet port 18. It will be understood that the sterilization additives may be introduced prior to pressurization and/or during pressure cycling. Prior to pressurization, additives are introduced directly into the mold reactor 22 prior to sealing and/or via the additive port 18. The sterilization additives are most preferably introduced during the cycling stages by measured addition to the additive port 18 at ambient pressures. The port 18 is subsequently sealed and the additive chamber is pressurized so that the additive may enter the mold reactor 22 without altering the internal pressure. The exact mechanism of addition may be modified such that the process is more efficient and/or convenient.

Following additive introduction, the mold reactor 22 may be repressurized to a desired pressure following introduction of the liquid additive therein. Such depressurization/repressurization with introduction of liquid additive may be repeated for any number of cycles that may be desired. The cycle of depressurization and repressurization as well as the introduction of the carbon dioxide and liquid additive may be automatically controlled via a controller screen which sequences the various valves discussed previously so as to achieve the desired pressure conditions and cycles.

In the treatment of "green state" materials it has been found that it is desirable to precisely control the pressurization and depressurization rates in the sterilization mold reactor. For the production of these molded products, the input or flow of $CO_2$ through valve 24 into the mold reactor 22 is regulated to at least 5 psi/second. Regulating the rate of pressurization is also intended to control mass flow (1000 mg/second) of $CO_2$ into the mold reactor 22. In the initial fill, the valve 24 is opened and allowed to flow at the regulated rate using the ambient pressure of the $CO_2$ supply from the gas cylinder 12. The $CO_2$ supply pressure can range from 75 psi to approximately 900 psi or greater. Once the pressure in reactor pressure vessel 22 reaches equilibrium with the $CO_2$ supply source pressure, the pumping of the $CO_2$ using the carbon dioxide booster 16 begins. The $CO_2$ booster rate of pressurization is regulated so as not to exceed 5 psi/second. Once the reactor pressure vessel 22 reaches its operating pressure of 1500 psi, the process is allowed to continue through its normal path. Upon completion of the desired time period at the operating temperature and pressure, depressurization of the mold reactor 22 then occurs. At this point the output valve 52 is opened enough that the rate of depressurization is regulated to at least 5 psi/second, preferably at least 25 psi/second, most preferably at least 75 psi/second. Regulating the rate of depressurization is also intended to control of mass flow of $CO_2$ out of the mold reactor 22. The rate of depressurization is controlled at this rate until the ambient pressure in the mold reactor 22 is zero or at equilibrium with the atmospheric pressure. Ambient conditions are generally zero psi and 25° C.

Most preferably periodic agitation to the contents of mold reactor 22 is effected using a vibrator 60 through the entire process. Intermittent or continuous agitation of the mold reactor 22 and its contents is performed by vibrating the mold reactor 22 during sterilization. Agitation enhances mass transfer of the carbon dioxide and additives by eliminating voids in the fluid such that the material in the mold being sterilized comes into more complete contact with sterilant. The specific means of agitation may be adjusted to accommodate the particular apparatus employed and to optimize sterilization times, temperatures, and pressure cycles. When sterilization is complete, the reactor pressure vessel 22 is depressurized, the magnetic driver 66 is stopped thereby stopping the stirring impeller 64, and the thus sterilized material removed by opening top 68 of reactor pressure vessel 22.

The present invention will be further understood after careful consideration is given to the following Example.

Example 1

The apparatus generally depicted in FIGS. 1 and 2 was employed for this Example. A sample of polyglycolide was placed in the perforated mold lined with Tyvek having an inner form in the shape of a disc. Peracetic acid (16 mL), was also charged into the mold reactor. The mold reactor was pressurized with $CO_2$ at a rate of 5 psi/second as discussed above and heated to 35° C. Stirring and agitation mechanisms were activated and the reactor vessel eventually reached 1500 psi. The process continued for 180 minutes while maintaining the vessel at 1500 psi and a temperature of 35° C. After 180 minutes the depressurization step began. During depressurization the $CO_2$ pressure was then regulated to drop to 0 psi at a rate of 50 psi/second. The mold reactor was opened, the mold was removed and opened and a sterilized solid disc was recovered.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the present invention.

What is claimed is:

1. A method of forming a sterilized implant comprising the steps of: (a) placing a charge of a moldable powder material in need of sterilization in a mold and locating the mold within a reactor, (b) regulating a pressurization rate of the mold in the reactor to bring the charge into contact with a sterilant fluid comprising $CO_2$ at or near its supercritical pressure and temperature conditions and a chemical sterilization additive, (c) maintaining said contact with the sterilant fluid under said temperature and pressure conditions for a time sufficient to achieve a 6-log reduction or greater in colony forming units (CFUs), and then (d) regulating a depressurization rate of the mold in the reactor until ambient operating conditions are reached, wherein by regulating the pressurization and depressurization rates, the moldable powder material is formed into a sterilized shaped article.

2. The method of claim 1, wherein the chemical sterilization additive is present in an amount of between about 0.001% to about 2.0% based on the total volume of the sterilant fluid.

3. The method of claim 1, wherein the chemical sterilization additive is selected from the group consisting of hydrogen peroxide, acetic acid, peracetic acid and trifluoroacetic acid and/or a mixture thereof.

4. The method of claim 1, wherein the moldable powder material is selected from metal powders; ceramic and glass powders, alumina, calcium phosphate, calcium carbonate, hydroxyapatite, silica, silicates, borosilicate; polylactide (PLA), polyglycolide (PGA), poly(lactide-co-glycolide) (PLGA), poly(e-caprolactone), polydioxanone, polyanhydride, dimethylene carbonate, poly(B-hydroxybutyrate) (PHB), poly(g-ethyl-glutamate), poly(DTH iminocarbonate), poly(bisphenol A iminocarbonate), poly(ortho ester), polycyanoacrylate, polyphosphazene, ethylene oxide block copolymers, polysaccharides, cellulose, chitin, dextran, natural polymers, fibrin, collagen, gelatin, hyaluronan, casein, polycarbonate, and poly(HEMA); monomers; resins; demineralized bone matrix, bone glue, crystalline small molecules; and mixtures thereof.

5. The method of claim 1, wherein the step of regulating the pressurization rate of the mold occurs at least 5 psi per second until operating conditions are reached sufficient to achieve molding, and the step of regulating the depressurization rate of the mold until ambient operating conditions are reached occurs at least 5 psi per second.

6. The method of claim 1, wherein the step of regulating the depressurization rate of the mold occurs at least 5 psi per second until ambient operating conditions are reached.

7. The method of claim 1, the step of regulating the depressurization rate of the mold until ambient operating conditions are reached occurs at least 75 psi per second.

8. The method of claim 1, wherein pressurization occurs until at least 1000 psi is reached.

9. The method of claim 1, wherein the pressure is maintained at least at 1000 psi for 20 to 720 minutes and then regulated depressurization occurs.

10. The method of claim 1, wherein depressurization occurs at a rate of 5 to 75 psi per second until ambient conditions are reached.

11. A method of forming a sterilized article comprising (a) placing a charge comprising a moldable powder material in a mold capable of allowing entry of a fluid during molding and locating the mold within a reactor, (b) contacting the moldable material with a sterilant fluid and regulating a pressurization rate of the mold to bring the moldable material into contact with the sterilant fluid comprising $CO_2$ at or near its supercritical pressure and temperature conditions and a chemical sterilization additive while in the reactor, (c) maintaining said contact with the sterilant fluid for a time period sufficient to achieve a degree of sterilization desired for the article, and then (d) regulating a depressurization rate of the mold while in the reactor until ambient operating conditions are reached, wherein by regulating the pressurization and depressurization rates, the moldable powder material is formed into a sterilized shaped article.

12. The method of claim 11, wherein the moldable powder material is selected from metal powders; ceramic and glass powders, alumina, calcium phosphate, calcium carbonate, hydroxyapatite, silica, silicates, borosilicate; polylactide (PLA), polyglycolide (PGA), poly(lactide-co-glycolide) (PLGA), poly(e-caprolactone), polydioxanone, polyanhydride, dimethylene carbonate, poly(B-hydroxybutyrate) (PHB), poly(g-ethyl-glutamate), poly(DTH iminocarbonate), poly(bisphenol A iminocarbonate), poly(ortho ester), polycyanoacrylate, polyphosphazene, ethylene oxide block copolymers, polysaccharides, cellulose, chitin, dextran, natural polymers, fibrin, collagen, gelatin, hyaluronan, casein, polycarbonate, and poly(HEMA); monomers; resins; demineralized bone matrix, bone glue, crystalline small molecules; and mixtures thereof.

13. A method of forming a molded article comprising (a) placing a charge of a moldable powder material in a mold capable of allowing entry of a fluid during molding and locating the mold within a reactor, (b) regulating a pressurization rate of the mold to bring the charge into contact with a sterilant fluid comprising $CO_2$ at or near its supercritical pressure and temperature conditions and a chemical sterilization additive while in the reactor, (c) maintaining said contact with the sterilant fluid under said temperature and pressure conditions for a time sufficient to achieve molding, and then (d) regulating a depressurization rate of the mold while in the reactor until ambient operating conditions are reached, wherein by regulating the pressurization and depressurization rates, the moldable powder material is formed into a molded article.

14. The method of claim 13, wherein the molded article is suitable for implanting in a human body.

15. The method of claim 13, wherein the moldable material is selected from metal powders; ceramic and glass powders, alumina, calcium phosphate, calcium carbonate, hydroxyapatite, silica, silicates, borosilicate; polylactide (PLA), polyglycolide (PGA), poly(lactide-co-glycolide) (PLGA), poly(e-caprolactone), polydioxanone, polyanhydride, dimethylene carbonate, poly(B-hydroxybutyrate) (PHB), poly(g-ethyl-glutamate), poly(DTH iminocarbonate), poly(bisphenol A iminocarbonate), poly(ortho ester), polycyanoacrylate, polyphosphazene, ethylene oxide block copolymers, polysaccharides, cellulose, chitin, dextran, natural polymers, fibrin, collagen, gelatin, hyaluronan, casein, polycarbonate, and poly(HEMA); monomers; resins; demineralized bone matrix, bone glue, crystalline small molecules; and mixtures thereof.

* * * * *